(12) United States Patent
Olson et al.

(10) Patent No.: US 8,634,927 B2
(45) Date of Patent: Jan. 21, 2014

(54) MEDICAL DEVICE RECHARGE SYSTEMS USING A CONTROLLER IN WIRELESS COMMUNICATION WITH A SEPARATE RECHARGE DEVICE

(75) Inventors: David P. Olson, Minnetrista, MN (US); Nathan A. Torgerson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 259 days.

(21) Appl. No.: 13/016,711

(22) Filed: Jan. 28, 2011

(65) Prior Publication Data

US 2012/0197351 A1 Aug. 2, 2012

(51) Int. Cl.
A61N 1/08 (2006.01)

(52) U.S. Cl.
USPC .......................................... 607/60

(58) Field of Classification Search
USPC .......................................... 607/60
See application file for complete search history.

(56) References Cited

U.S. PATENT DOCUMENTS

| | | |
|---|---|---|
| 5,107,833 A | 4/1992 | Barsness |
| 5,733,313 A | 3/1998 | Barreras et al. |
| 5,735,887 A | 4/1998 | Barreras et al. |
| 5,755,748 A | 5/1998 | Borza |
| 6,212,430 B1 | 4/2001 | Kung |
| 6,263,247 B1 | 7/2001 | Mueller et al. |
| 6,345,203 B1 | 2/2002 | Mueller et al. |
| 6,430,444 B1 | 8/2002 | Borza |
| 6,631,296 B1 | 10/2003 | Parramon et al. |
| 7,138,902 B2 | 11/2006 | Menard |
| 7,406,105 B2 | 7/2008 | Delmain et al. |
| 7,471,986 B2 | 12/2008 | Hatlestad |
| 7,664,553 B2 | 2/2010 | Roberts |
| 2003/0078634 A1 | 4/2003 | Schulman et al. |
| 2003/0114898 A1 | 6/2003 | Von Arx et al. |
| 2007/0060980 A1 | 3/2007 | Strother |
| 2007/0129767 A1 | 6/2007 | Wahlstrand |
| 2007/0150019 A1 | 6/2007 | Youker et al. |
| 2008/0058900 A1 | 3/2008 | Berthelsdorf et al. |

(Continued)

FOREIGN PATENT DOCUMENTS

| | | |
|---|---|---|
| EP | 2092958 | 8/2009 |
| WO | 2003039652 B1 | 1/2004 |

(Continued)

OTHER PUBLICATIONS

Partial International Search Report issued in PCT/US2011/054002 on Dec. 23, 2011.

(Continued)

*Primary Examiner* — Eric D. Bertram
(74) *Attorney, Agent, or Firm* — Withers & Keys, LLC (57) ABSTRACT

Medical device recharging systems include a controller and a separate recharge device that communicate wirelessly together to provide recharging to an implantable medical device. Either the controller or the recharge device may also communicate wirelessly with the implantable medical device to obtain recharge status and other information. There may be multiple recharge devices present within communication range of the controller, and the controller may determine which recharge device to activate depending upon proximity of each recharge device to the implantable medical device. The controller may allow the recharge device that is active at any given time to change so that the patient having the implantable medical device can move about in the area where the recharge devices are located while recharging continues.

21 Claims, 8 Drawing Sheets

(56) References Cited

U.S. PATENT DOCUMENTS

| | | | |
|---|---|---|---|
| 2008/0109051 A1 | 5/2008 | Splinter et al. | |
| 2008/0300660 A1 | 12/2008 | John | |
| 2009/0073991 A1 | 3/2009 | Landrum et al. | |
| 2009/0118796 A1 | 5/2009 | Chen et al. | |
| 2009/0182388 A1 | 7/2009 | Von Arx et al. | |
| 2009/0259273 A1 | 10/2009 | Figueiredo et al. | |
| 2009/0270948 A1 | 10/2009 | Nghiem et al. | |
| 2010/0114216 A1 | 5/2010 | Krause et al. | |
| 2010/0305663 A1* | 12/2010 | Aghassian | 607/61 |

FOREIGN PATENT DOCUMENTS

| | | |
|---|---|---|
| WO | 2008069829 | 6/2008 |
| WO | 2009055203 | 4/2009 |
| WO | 2009055579 | 4/2009 |
| WO | 2010051485 | 5/2010 |
| WO | 2011/034681 | 3/2011 |
| WO | 2011/059643 | 5/2011 |
| WO | 2011079309 | 6/2011 |

OTHER PUBLICATIONS

International Search Report and Written Opinion of the International Search Authority, issued Jul. 18, 2012, in PCT application, PCT/US2011/064480.

U.S. Appl. No. 13/016,763, filed Jan. 28, 2011.

U.S. Appl. No. 13/016,793, filed Jan. 28, 2011.

International Search Report, issued in PCT/US2011/054002 on Apr. 19, 2012.

Written Opinion of the International Searching Authority, issued in PCT/US2011/054002 on Apr. 19, 2012.

International Search Report and Written Opinion issued in PCT/US2011/051921, Feb. 19, 2013.

Budgett, David, M. et al., "Novel Technology for the Provision of Power to Implantable Physiological Devices", Journal of Applied Physiology, vol. 102, No. 4, pp. 1658-1663, Apr. 1, 2007.

U.S. Appl. No. 13/016,793 Restriction Requirement dated Sep. 26, 2012.

U.S. Appl. No. 13/016,793 Response to Restriction Requirement filed Oct. 26, 2012.

* cited by examiner

MEDICAL DEVICE RECHARGE SYSTEMS USING A CONTROLLER IN WIRELESS COMMUNICATION WITH A SEPARATE RECHARGE DEVICE

TECHNICAL FIELD

Embodiments relate to medical systems that include a rechargeable medical device. More particularly, embodiments relate to medical systems that include a controller that wirelessly communicates with a separate recharge device that delivers the recharge energy to the rechargeable medical device.

BACKGROUND

Medical systems that include medical devices having rechargeable batteries typically utilize near field telemetry for communications with a controller. The controller may also include recharge functions so that the controller may utilize the same telemetry head to transfer the recharge energy to the medical device in addition to exchanging telemetry communications.

This configuration provides a workable solution but there may be drawbacks. In particular, a telemetry head extending from the controller may be manually held in place relative to the medical device during the recharge process as well as during telemetry communications. A cord from the telemetry head to the controller may be a burden to the patient as the cord may be an annoyance and may need to route through clothes of the patient to provide proper connectivity.

This configuration may provide additional drawbacks. For instance, in some cases the transfer of recharge energy may pause during near field telemetry communications being used to monitor the recharge process thereby further prolonging the recharge process. As another drawback, the controller may be relatively expensive, especially considering the control and recharge functions are both included, such that having multiple devices capable of providing the recharge function calls for multiple controllers which may be costly to the patient.

SUMMARY

Embodiments address issues such as these and others by providing medical systems that include a controller that is in wireless communication with a separate recharge device. Accordingly, no cords are needed between the controller and a recharge head. Furthermore, multiple recharge devices may be used with a single controller. In some cases, the controller may be provided with wireless communication with the medical device in addition to the wireless communication with the recharge device so that the recharge device does not communicate with the medical device.

Embodiments include a method of recharging an implantable medical device that involves initiating wireless communications between a first controller and a first recharge device that provide first recharge instructions from the first controller to the first recharge device to control recharging. The method further involves transferring recharge energy from the first recharge device to the implantable medical device in accordance with the first recharge instructions.

Embodiments include a medical system that includes a first controller having a wireless communication circuit. The medical system further includes a first recharge device having a wireless communication circuit in wireless communication with the wireless communication circuit of the first controller and having a wireless recharge circuit. The first recharge device receives first recharge instructions from the first controller and generates recharge energy in the recharge circuit based on the first recharge instructions. The medical system further includes an implantable medical device having a wireless recharge circuit having a wireless near field coupling to the wireless recharge circuit of the first recharge device to receive recharge energy from the first recharge device.

Embodiments include a method of recharging an implantable medical device that involves sensing the presence of a first recharge device. The method further involves, in response to sensing the presence of the first recharge device, instructing the first recharge device to begin the transfer of recharge energy from the first recharge device to the implantable medical device.

Embodiments include a medical system that includes an implantable medical device, a first recharge device, and a controller. The controller senses the presence of the first recharge device and in response to sensing the presence of the first recharge device, instructs the first recharge device to begin the transfer of recharge energy from the first recharge device to the implantable medical device.

Embodiments include a method of recharging an implantable medical device. The method involves initiating wireless communications between a first controller and the implantable medical device that provide first recharge instructions from the first controller to the implantable medical device to control recharging. The method further involves initiating wireless communications between the implantable medical device and a recharge device to provide the first recharge instructions from the implantable medical device to the first recharge device. The method also involves transferring recharge energy from the first recharge device to the implantable medical device in accordance with the first recharge instructions.

DETAILED DESCRIPTION

Embodiments provide an external controller with a wireless communication link to an external recharge device. The external recharge device provides a wireless coupling to an implantable medical device (IMD) to transfer recharge energy to the IMD. The external controller and/or the external recharge device may provide a wireless communication link to the IMD. The controller and IMD may be used in conjunction with multiple recharge devices, and the controller may initiate recharge of the IMD using a recharge device that is in closest proximity.

Figure 1:
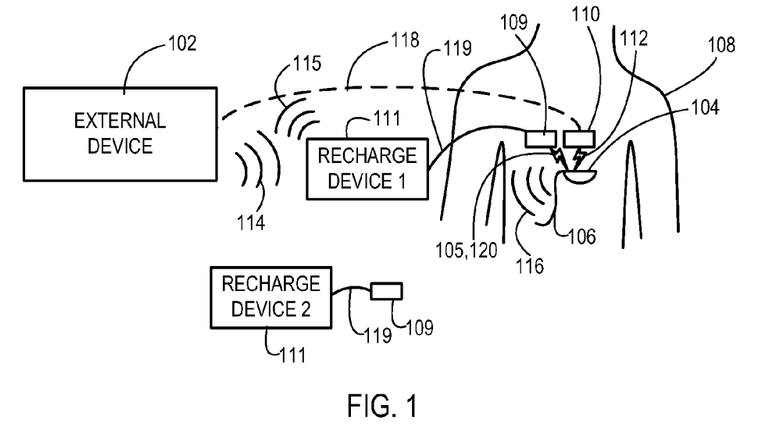
FIG. 1 shows an example of a medical system with recharge abilities according to various embodiments.

FIG. 1 shows an environment that includes an external controller 102, such as a clinician programmer or a patient programmer that is nearby a patient 108 who has an IMD 104. The IMD 104 may be implanted within or mounted externally to the body 108 and may perform one or more medical tasks such as cardiac or neurological stimulation, physiological sensing, drug infusion, and the like. The IMD 104 may include components 106 such as stimulation or sensing leads or drug delivery catheters that extend from the IMD 104 and terminate at the target area of the body 108.

The patient 108 ultimately wants the IMD 104 to be recharged so that medical therapy can continue. The controller 102 may provide various functions including a recharge function whereby a recharge session is established in order to transfer recharge energy between an external recharge device 111 and the IMD 104. During the recharge session, recharge energy is provided while a wireless communication session, such as a far field communication session for example, is also conducted to allow the controller 102 to receive feedback about charging status from the IMD 104. The communication session with the IMD 104 may be directly with the controller 102 or directly with the external recharge device 111 if the external recharge device 111 is so equipped or with both the controller 102 and the recharger 111. In the two latter cases, the controller 102 then conducts a wireless communication session, such as a far field communication session for example, with the external recharge device 111 to instruct the external recharge device 111 to provide recharge energy as is appropriate and also to obtain information regarding the recharge status that has been provided by the IMD 102.

In some embodiments, the controller 102 communicates with the IMD 104 during a recharge session through a wireless communication session such as by utilizing far field signals 114 sent by the controller 102, for example, to obtain recharge status information from the IMD 104. The controller 102 may also communicate via wireless communication signals, such as far field communication signals 114 for example, with the recharge device 111 such as to provide instructions to the recharge device 111 to begin transferring recharge energy, and the recharge device 111 may communicate acknowledgement of the instructions to the controller 102 via the wireless communication signals, such as far field communication signals 115 for example. The IMD 104 may communicate with the controller 102 by sending wireless communication signals, such as far field communication signals 116 for example.

In other embodiments, the recharge device 111 may communicate with the IMD 104 via the wireless communication signals such as the far field signals 115 to obtain recharge status information from the IMD 104. The recharge device may then communicate that information via the wireless communication signals such as the far field signals 115 to the controller 102 rather than the controller 102 communicating directly with the IMD 104 for the recharge status information. The IMD 104 may communicate with the recharge device 111 by sending the wireless communication signals such as the far field signals 116 or via a near field communication link.

In another embodiment, the controller 102 may communicate with the IMD 104 via the wireless communication signals such as far field communication signals 115 or via near field proximity signals to obtain recharge status information from the IMD 104 and send recharge settings for the recharge device to the IMD 104. The recharge device 111 may then communicate with the IMD 104 via a wireless communication link such as a near field communication link in order to receive information about altering the recharge which was stored in the IMD 104 by the controller 102.

The far field signals 114, 115, and 116 that may be used in some examples may be radio frequency (RF) signals such as those of the Medical Implant Communications Service (MICS) band that spans 402-405 MHz, the Industrial, Scientific, and Medical (ISM) band, or the short range device (SRD) band. These far field communication signals, particularly for the communications between the controller 102 and the recharge device 111, may utilize protocols such as the Bluetooth® protocol that spans 2402-2480 MHz to exchange information. Far field telemetry communications are those where a wave is propagated and that wave may be used to carry the communications as opposed to relying on an inductive coupling. Thus, far field telemetry communications are those where the signal may travel a distance in excess of one wavelength of the carrier frequency.

While the single IMD 104 is shown in FIG. 1, it will be appreciated that there may be other IMDs and/or other external devices nearby and in range of the far field signals 114 of the external device 102 and/or the far field signals 115 of the recharge device 111. Where the IMD 104 is bonded via a shared key or other technique to the controller 102 and/or the recharge device 111, then the bond allows the far field communication session with the correct IMD 104 to be initiated regardless of the presence of other IMDs. In some situations such as where a new controller 102 or recharge device 111 is being used to communicate with the IMD 104 for the first time such that no bond exists, the controller 102 and/or recharge device 111 may not be aware of identification information of the intended IMD 104 in advance such that the controller 102 and/or recharge device 111 cannot immediately discern far field communications of the intended IMD 104 relative to far field communications of other IMDs such that an initial proximity based bonding process may be used. A bond may then be created between the IMD 104 and the controller 102 and/or recharge device 111 by sharing an encryption key or other similar information used to establish the bond.

Physical proximity can be established to allow proximity communication 112 to occur between the controller 102 and the intended IMD 104 or to allow a proximity communication 105 to occur between the recharge device 111 and the intended IMD 104. Physical proximity refers to the intended IMD 104 being positioned closely to the external device 102 to the extent that an observer such as a clinician can confirm that the intended IMD 104 is the only IMD that can be responsive to proximity communications. Where the proximity communication is a near field signal from the proximity telemetry, the proximity telemetry communications are those where the signal may travel a distance less than one wavelength of the carrier frequency, which is typically an inductively coupled signal transfer. For proximity telemetry, the external device 102 must be within physical proximity of the IMD (i.e., within the patient's "personal space") for the IMD to communicate with the external device. This is opposed to far field communications wherein external device 102 may, but need not, be within physical proximity of the IMD to communicate with the IMD.

Therefore, a procedure is provided that utilizes this physical proximity at the initiation of the far field communication session to avoid the controller 102 and/or recharge device 111 conducting a far field communication session with an unintended nearby IMD while the recharge device 111 is recharging the intended IMD 104. To allow the controller 102 and/or recharge device 111 to select the intended IMD 104 for far field communication during a recharge session and avoid selecting an unintended nearby IMD, the proximity communication signals 105 or 112 may be exchanged between a proximity communicator 110 of an embodiment of the controller 102 or a proximity communicator 109 of an embodiment of the recharge device 111 and the IMD 104 during the establishment of the far field communication session. The proximity communicator 110 and/or the proximity communicator 109 may be contained within the controller 102 or recharge device 111, respectively rather than being tethered.

The proximity communicator 109 or 110 may be of various forms and may be a separate component of the recharge device 111 or controller 102 or be integrated with the recharge device 111 or controller 102, or a combination of both. For instance, the proximity communicator 109 or 110 may be a near field telemetry head that is tethered to the recharge device 111 by a communication path 119 or to the controller 102 by a communication path 118. The communication path 118 or 119 may be of various forms such as a cable or a wireless connection.

For embodiments of the recharge device 111, the proximity communicator 109 may also integrate recharge circuitry including a recharge coil that inductively couples to a coil of the IMD 104 to inductively transfer energy. Thus, a single tool may be placed in physical proximity of the patient 108 in order to establish a form of proximity communication and to delivery recharge energy. The recharge energy may be sourced from an on-board power supply of the recharge device 111 where it is fed to the proximity communicator 109 for delivery to the IMD 104.

Additionally, according to some embodiments, the proximity communicator 109 or other source of near field telemetry of the recharge device 111 may be used to communicate with the IMD 104 via proximity signals 120 rather than using far field communication signals 115 and 116. The recharge device 111 may use the proximity signals 120 to obtain the recharge status information from the IMD 104 which can then be provided to the controller 102 via the far field communication signals 115.

In some embodiments, the controller 102 may be paired to a single recharge device 111. However, in other embodiments, the controller 102 may be paired to multiple recharge devices 111 where multiple recharge devices 111 may be in the general vicinity of the controller 102 and IMD 104 as shown in FIG. 1. Thus, the controller 102 may communicate with a first recharge device 111 for one recharge session and may communicate with a second recharged device 111 for a different recharge session, where the patient is located closer to the first or second recharge devices for any particular recharge session. Furthermore, as discussed below, the controller 102 may allow the patient to roam about during a recharge session whereby the controller 102 activates and deactivates first and second recharge devices 111 depending upon which recharge device 111 is in closest proximity to the IMD 104 of the patient at any given time during a recharge session.

Figure 2:
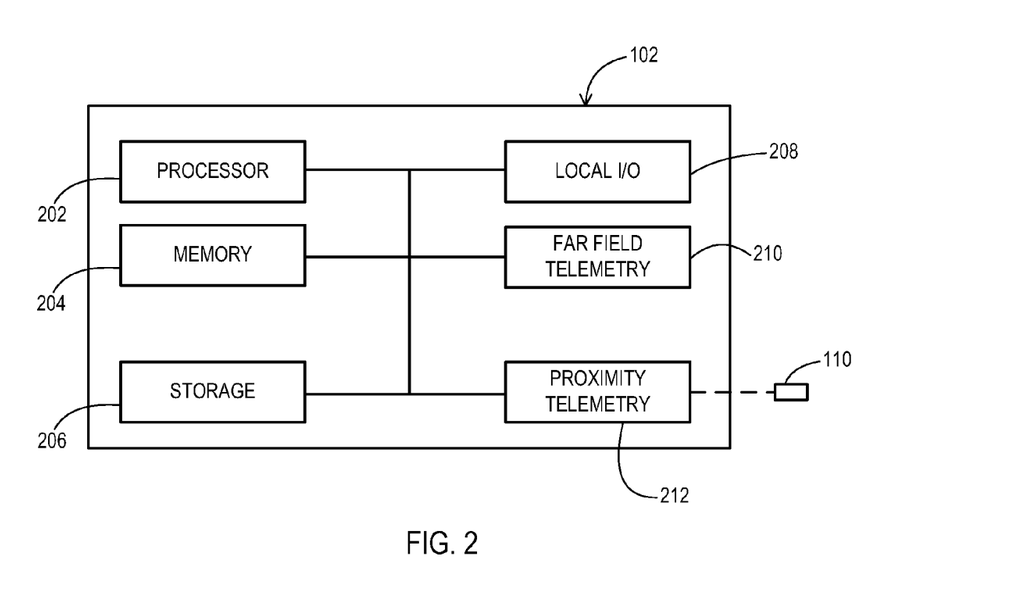
FIG. 2 shows an example of components of an external controller of the medical system.

FIG. 2 shows components of one example of the controller 102. The controller 102 includes a processor 202, a memory 204, and a storage device 206. The controller 102 may also include local input/output (I/O) ports 208 such as to provide local screen displays and to receive user input via keyboard, mouse, and so forth. For examples where communication with either the recharger 111 and/or the IMD 104 is via far field communications, the controller 102 also includes far field communication circuitry 210 used to establish the far field communication session with the recharge device 111 and/or the IMD 104. The far field communication circuitry 210 may drive a signal propagation tool such as an RF antenna. The signal propagation tool may be included within the proximity communicator 110 so that the far field communication circuitry 210 instructs the signal propagation tool over the connection 118 or the signal propagation tool may be a separate external component or housed within the controller 102.

In addition to the far field communication circuitry 210, some embodiments of the controller 102 may also include a proximity communication circuitry 212, particularly those embodiments where the controller 102 communicates directly with the IMD 104 and/or recharger 111 via far field communications. The proximity communication circuitry 212 may be of various forms to interact with the IMD 104 via the proximity communicator 110 so as to ensure that the controller 102 is communicating with the intended IMD 104 via the far field communication signals 114, 116. The proximity communicator 110 may include a near field inductive driver circuit, a signal generator for producing audible tones, a motion signal generator for driving a body thump device, a field producing circuit for driving an electromagnet, and the like that are responsive to the data commands. The proximity communication circuitry 310 may include near field telemetry or may omit such telemetry for examples where information is exchanged in other manners or exclusively via a far field communication.

The controller 102 may include additional communication capabilities that may be provided by far field communication circuitry 210 or by additional communication circuitry. For instance, the controller 102 may include Wi-Fi connectivity, public switched telephone network connectivity, and so forth to allow for remote communication, particularly where the controller 102 is a patient controlled device.

The memory 204 may be used to store information in use by the processor 202. For instance, the memory 204 may store therapy parameters that are input by a clinician or patient that are to be loaded into the IMD 104. The memory 204 may also store programming that is used by the processor 202 to control an IMD selection procedure of the controller 102, to control a recharge device selection procedure of the controller 102 which is discussed below, and to control the delivery of the recharge energy by the recharge device 111 such as based on feedback received from the IMD 104 during the recharge process. The memory 204 may be of various types, such as volatile, non-volatile, or a combination of the two.

The storage device 206 may be used to store information for a long term and may be of various types such as non-volatile so that the information is retained when the controller 102 is powered off. The storage device 206 may also store programming for the processor 202 that is implemented to control the IMD selection procedure, the recharge device selection procedure, and the delivery of recharge energy. Examples of the storage device 206 include electronic, magnetic, and optical drives. The storage device 206 and the memory 204 are both examples of computer readable media that may store information in the form of computer programming, data structures, and the like.

The processor 202 performs logical operations to provide a sequence of far field communications and may also provide a sequence of proximity communications for embodiments where the controller 102 may communicate directly with the IMD 104. The logical operations may allow the controller 102 to select the proper recharge device 111 at any given time for a recharge session, and to control delivery of recharge energy during the recharge session. Examples of such operations are discussed below in relation to FIG. 6. The processor 202 may be of various forms. For instance, the processor 202 may be a general-purpose programmable processor that executes software that is stored on the storage device 206 or elsewhere. Other examples include a dedicated purpose hardware circuit or hard-wired digital logic. The processor 202 may be multiple separate components or processors, dedicated hardware/state machine, and the like. The processor 202 may communicate with the various other components through one or more data buses.

Figure 3:
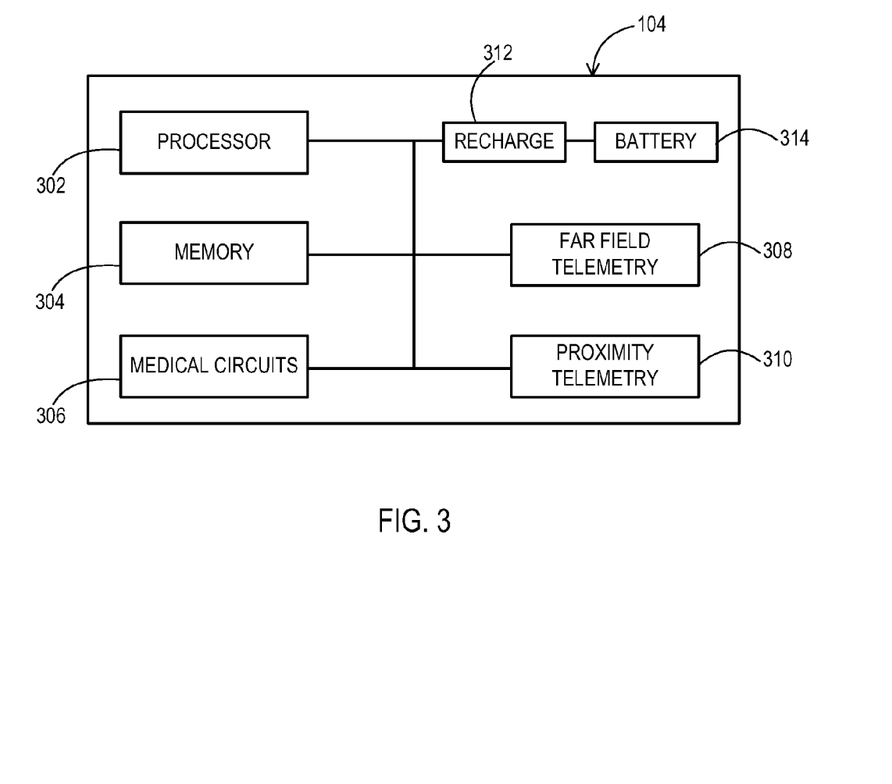
FIG. 3 shows an example of components of an implantable medical device of the medical system.

FIG. 3 shows components of one example of the IMD 104 to be recharged. The IMD 104 includes a processor 302 and a memory 304. The IMD 104 also includes medical circuitry 306 that performs a medical task such as stimulation, drug delivery, monitoring, and the like. The IMD 104 may also include far field communication circuitry 308 used to establish the far field communication session with the controller 102 and/or recharge device 111. The far field communication circuitry 308 may drive a signal propagation tool such as an integral RF antenna.

In addition to the far field communication circuitry 308, the IMD 104 may also include proximity communication circuitry 310. The proximity communication circuitry 310 may be of various forms where for a given system, the type of proximity communication circuitry 310 matches the type of proximity communicator 110 that the recharge device 111 includes. Accordingly, the proximity communication circuitry 310 may be a near field inductive receiver, a microphone for receiving audible tones, an accelerometer or other vibration detection device, a field operable switch such as a magnetic reed switch, and the like. The proximity communication circuitry 310 may include near field telemetry or may omit such telemetry for examples where information is exchanged in other manners or exclusively via a far field communication.

The IMD 104 also includes a rechargeable battery 314 and a recharge circuit 312 coupled to the battery 314. The recharge circuit 312 may include a coil that inductively couples to the coil of the recharge circuit 214 of the recharge device 111. The recharge circuit 312 may utilize a dedicated coil or may utilize a coil that is also used by the proximity communication circuit 310. The recharge circuit 312 may include rectification, filtering, voltage/current limiting, and the like so as to provide an appropriate form of recharge power to the battery 314.

The memory 304 may be used to store information in use by the processor 302 such as programming and data values. The memory 304 may store additional information including therapy parameters that are used to control the medical circuitry 306 as well as recharge parameters that are used to control the recharge circuitry 312. The memory 304 may be of various types such as volatile, non-volatile, or a combination of the two. The memory 304 is also an example of computer readable media that may store information in the form of computer programming, data structures, and the like.

Figure 7A:
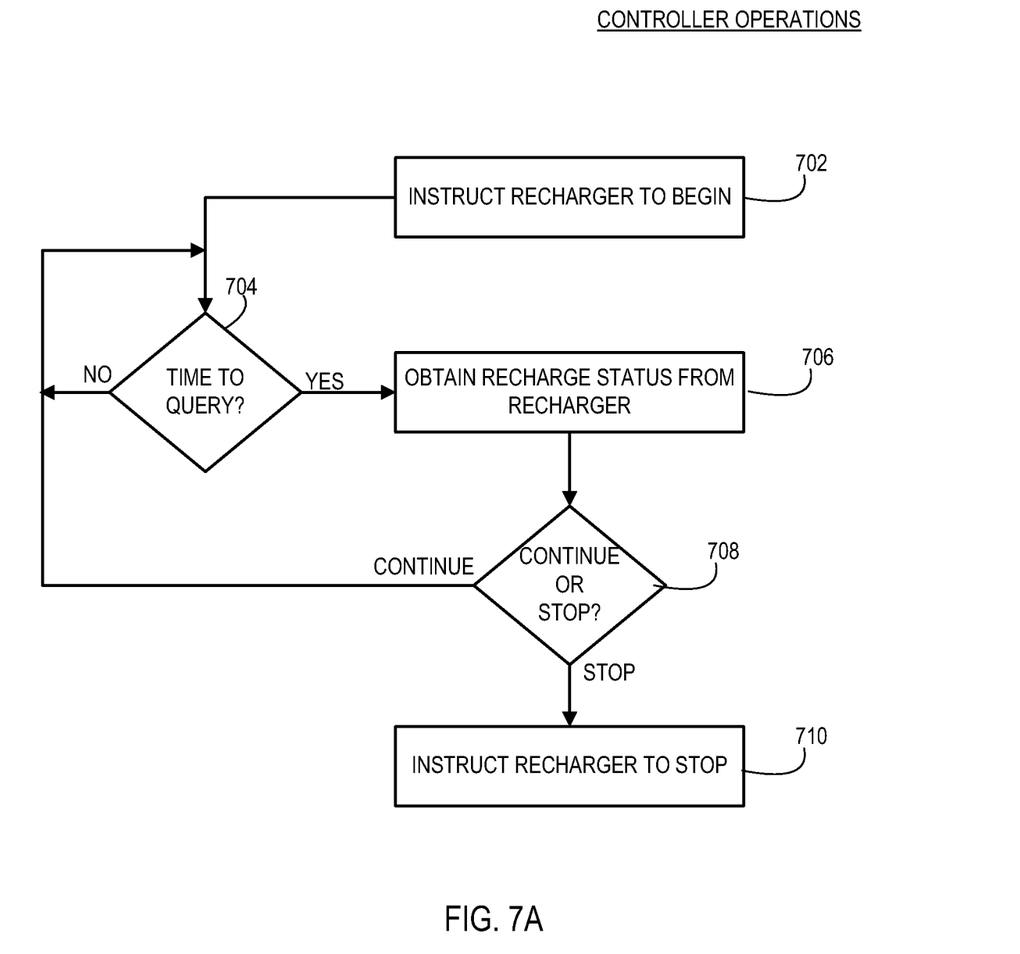
FIG. 7A shows a second example of operations of the external controller to conduct a recharge session.

The processor 302 performs logical operations to provide a sequence of far field and proximity communications, and to control delivery of received recharge energy to the battery 314. An example of these logical operations is discussed in more detail below with reference to FIG. 7. The processor 302 may be of various forms like those discussed above for the processor 202 of the external device 102 and as discussed above may be multiple separate components or processors, dedicated hardware/state machine, and the like. The processor 302 may communicate with the various other components through one or more data buses.

Figure 4:
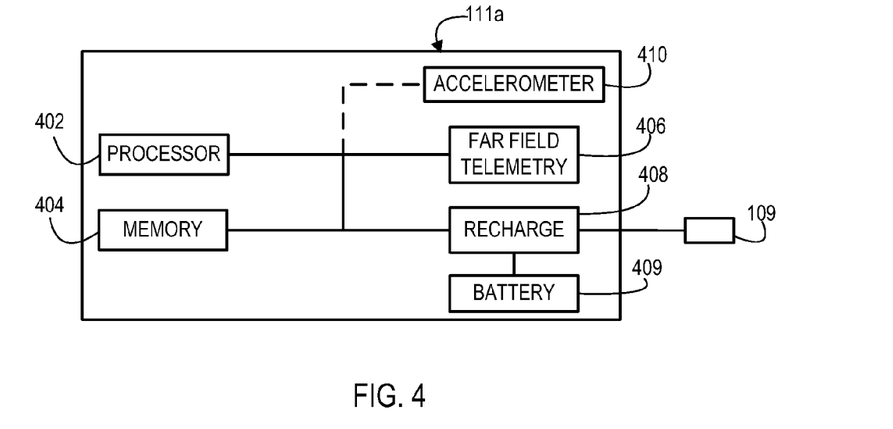
FIG. 4 shows a first example of components of an external recharge device of the medical system.

FIG. 4 shows components of one embodiment of the recharge device 111a. This embodiment 111a may rely on the controller 102 to utilize proximity communications with the IMD 104 to confirm that the far field communications of either the controller 102 or the recharge device 111a are being exchanged with the correct IMD 104. Additionally or alternatively, this embodiment 111a may rely on the controller 102 to communicate directly with the IMD 104 via far field communications such that the recharge device 111 communicates via far field communications with the controller 102.

The recharge device 111a of FIG. 4 may include a processor 402 and a memory 404. The recharge device 111a may also includes far field communication circuitry 406 used to establish the far field communication session with the controller 102 and/or the IMD 104. The far field communication circuitry 406 may drive a signal propagation tool such as an integral RF antenna.

The recharge device 111 also includes a battery 409 that is either rechargeable or replaceable and a recharge circuit 408 coupled to the battery 409. The recharge circuit 408 may include a coil that inductively couples to the coil of the recharge circuit 312 of the IMD 104. The recharge circuit 408 generates recharge waveforms to inductively transfer energy to the IMD 104. The recharge circuit 408, for example, may include a coil that is driven by a waveform generator that receives energy from the battery 409. The recharge circuit 408 may include filtering, voltage/current limiting, and the like so as to emit an appropriate form of recharge power to the IMD 104. The recharge circuit 408 may drive the proximity communicator 109 which in this embodiment is being used solely for the transfer of recharge energy to the IMD 104. While the proximity communicator 109 has been shown in FIGS. 1 and 4 as being tethered to the recharge device 111, the proximity communicator 109 may be a component housed within the recharge device 111. Furthermore, in some embodiments the recharge device 111 may be entirely self-contained such that the recharge device 111 can be worn by the patient while providing the transfer of recharge energy.

This embodiment 111a may also include other features such as an accelerometer 410. The accelerometer 410 may be included so that a signal may be generated that is representative of movement of the recharge device 111a. As discussed below, this signal representative of movement may be communicated to the controller 102 to allow the controller to determine whether a particular recharge device 111a is in the closest proximity to the IMD 104 and is therefore the most appropriate choice for providing recharge energy to the IMD 104. In the simplest forms of the recharge device 111a, this accelerometer is omitted in favor of other techniques that the controller 102 may use to determine that the recharge device 111a should begin providing recharge energy.

As an example where the accelerometer 410 may be used, the recharger 111a may not be attached to the patient but may be in a location that the IMD 104 would have proximal contact with the recharger 111a sometime during the day, such as at a chair or bed. The movement detected by the accelerometer 410 is an indication to the recharger 111a that the IMD 104 may be close to the recharger 111a, and the recharger 111a can exit a low power state and attempt to communicate with the IMD 104 and/or controller 102. If the controller 102 is present, the recharger 111a may then attempt to recharge the IMD 104 under the direction of the controller 102.

The memory 404 may be used to store information in use by the processor 402 such as programming and data values.

The memory 404 may store additional information including recharge parameters that are used to control the recharge circuitry 408. The memory 404 may be of various types such as volatile, non-volatile, or a combination of the two. The memory 404 is also an example of computer readable media that may store information in the form of computer programming, data structures, and the like.

The processor 402 performs logical operations to provide a sequence of far field communications and to control delivery of recharge energy by the recharge circuit 408. An example of these logical operations is discussed in more detail below with reference to FIG. 6. The processor 402 may be of various forms like those discussed above for the processor 202 of the controller 102 and as discussed above may be multiple separate components or processors, dedicated hardware/state machine, and the like. The processor 402 may communicate with the various other components through one or more data buses.

Figure 5:
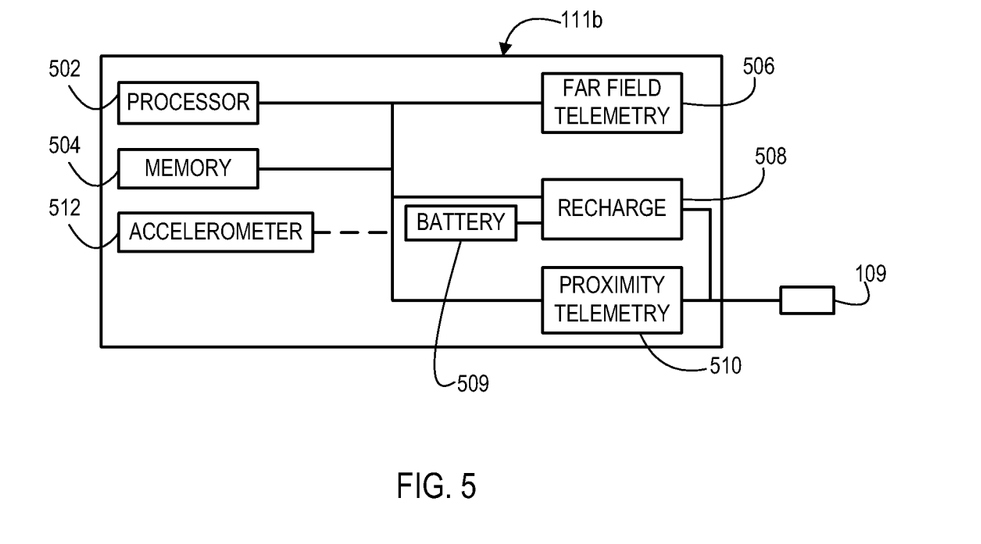
FIG. 5 shows a second example of components of an external recharge device of the medical system.

FIG. 5 shows components of another embodiment of the recharge device 111b. This embodiment 111b may utilize proximity communications with the IMD 104 to confirm that the far field communications of either the controller 102 or the recharge device 111b are being exchanged with the correct IMD 104. Additionally or alternatively, this embodiment 111b may utilize either far field communications or proximity communications to obtain recharge status information from the IMD 104.

The recharge device 111b of FIG. 5 may include a processor 502 and a memory 504. The recharge device 111b may also includes far field communication circuitry 506 used to establish the far field communication session with the controller 102 and/or the IMD 104. The far field communication circuitry 506 may drive a signal propagation tool such as an integral RF antenna.

The recharge device 111b also includes a battery 509 that is either rechargeable or replaceable and a recharge circuit 508 coupled to the battery 509. The recharge circuit 508 may include a coil that inductively couples to the coil of the recharge circuit 312 of the IMD 104. The recharge circuit 508 generates recharge waveforms to inductively transfer energy to the IMD 104. The recharge circuit 508, for example, may include a coil that is driven by a waveform generator that receives energy from the battery 509. The recharge circuit 508 may include filtering, voltage/current limiting, and the like so as to emit an appropriate form of recharge power to the IMD 104. The recharge circuit 508 may drive the proximity communicator 109 to provide the transfer of recharge energy to the IMD 104.

In addition to the far field communication circuitry 506, the recharge device 111b may also include proximity communicator circuitry 510 that drives the proximity communicator 109 to provide proximity communications with the IMD 104. As discussed above, these proximity communications may be used to ensure that the far field communications are being exchanged with the correct IMD 104 and to create a bond with the IMD 104. The proximity communicator circuitry 510 may be of various forms where for a given system, the type of proximity communicator circuitry 510 matches the type of proximity communication circuitry 310 that the IMD 104 includes. Accordingly, the proximity communicator circuitry 510 may be a near field inductive transmitter, a speaker for producing audible tones, a magnet, and the like.

This embodiment 111b may also include other features such as an accelerometer 512. The accelerometer 512 may be included so that a signal may be generated that is representative of movement of the recharge device 111b. As discussed below, this signal representative of movement may be communicated to the controller 102 to allow the controller to determine whether a particular recharge device 111b is in the closest proximity to the IMD 104 and is therefore the most appropriate choice for providing recharge energy to the IMD 104.

The memory 504 may be used to store information in use by the processor 502 such as programming and data values. The memory 504 may store additional information including recharge parameters that are used to control the recharge circuitry 508. The memory 504 may be of various types such as volatile, non-volatile, or a combination of the two. The memory 504 is also an example of computer readable media that may store information in the form of computer programming, data structures, and the like.

The processor 502 performs logical operations to provide a sequence of far field communications, a sequence of proximity communications, and to control delivery of recharge energy by the recharge circuit 508. An example of these logical operations is discussed in more detail below with reference to FIGS. 6-7B. The processor 502 may be of various forms like those discussed above for the processor 202 of the controller 102 and as discussed above may be multiple separate components or processors, dedicated hardware/state machine, and the like. The processor 502 may communicate with the various other components through one or more data buses.

Figure 6:
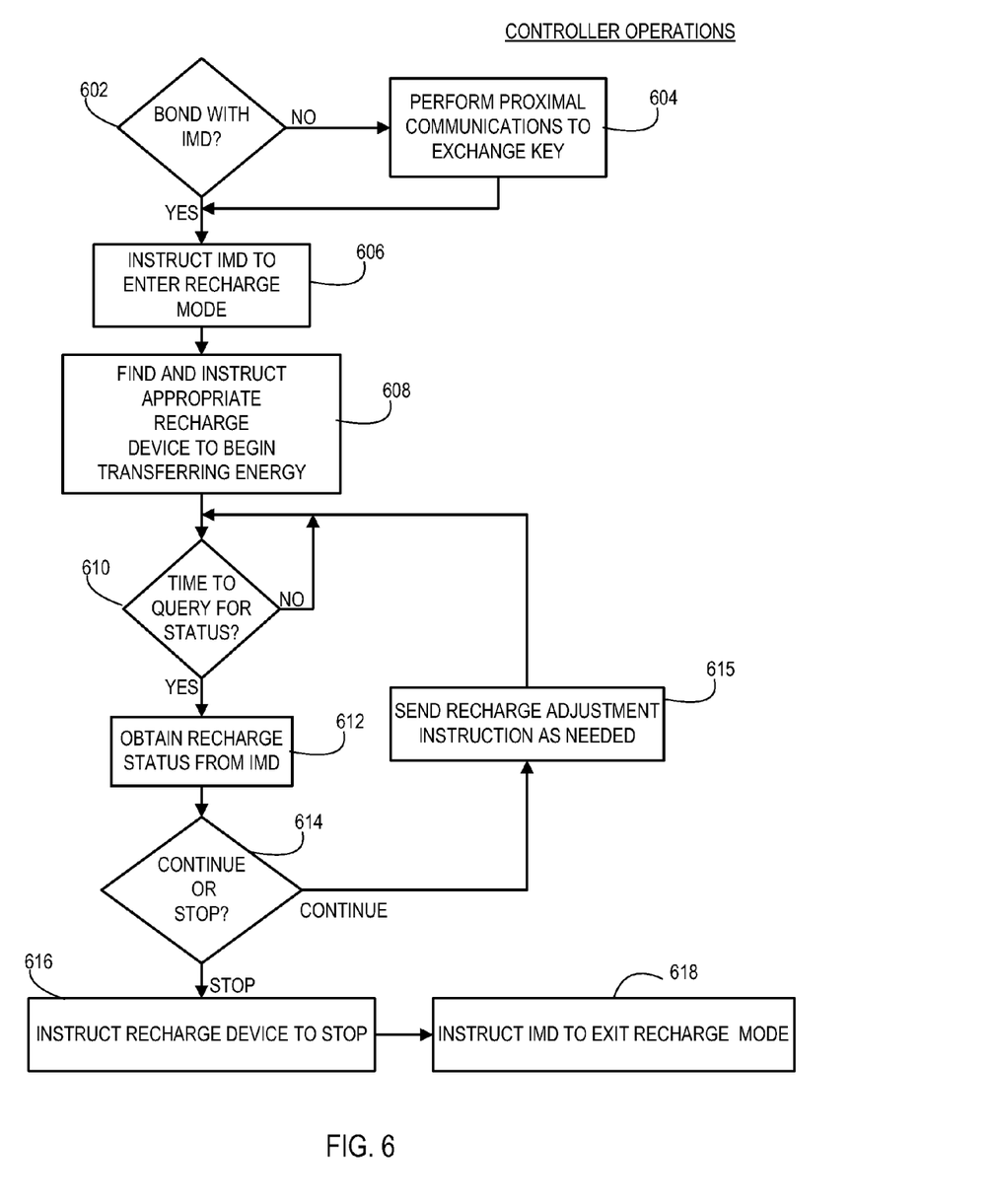
FIG. 6 shows a first example of operations of the external controller to conduct a recharge session.

FIG. 6 shows a set of logical operations that may be performed by the controller 102 in relation to one or more recharge devices 111 within far field communication range, or in some cases near field communication range of the controller 102 and the IMD 104 to be recharged to establish a recharge session. In this example, the controller 102 maintains wireless communications such as far field or near field communications with both the recharge device 111 and the IMD 104.

Initially in this example, the controller 102 discovers the presence of and IMDs including the IMD 104 and detects whether the IMD 104 being communicated with is the intended IMD to be recharged and/or has already been bonded to the controller 102 at a query operation 602. If the IMD being communicated with via the wireless communications is not already bonded as it does not have a communication key already shared with it by the controller 102, the controller 102 may then initiate proximal communications at communication operation 604. Here the controller 102 can detect whether the IMD 104 which is receiving the proximal communications is also receiving the wireless communications to confirm that the wireless communications are with the correct IMD 104, particularly where the wireless communications are far field communications. Once that has been confirmed, the controller 102 may then share the communication key with the IMD 104 such as over the proximal communication link so as to create the bond with the IMD 104.

In some embodiments, the controller 102 sends an instruction to the IMD 104 to enter a recharge mode at an instruction operation 606 so that the IMD 104 may begin receiving recharge energy and allowing it to pass through any rectification, filters, regulators and the like and ultimately to the battery 314. In some embodiments, the IMD 104 may be configured to always receive transferred energy to send to the battery 314 such that the instruction operation 606 is not implemented. Furthermore, for embodiments where the controller 102 is already bonded to the IMD 104, the logical operations may start at the instruction operation 606 or may start at a subsequent operation such as where the IMD 104 is always configured to receive the transfer of energy.

The subsequent operation for the controller 102 is to instruct an appropriate recharge device 111 over a wireless communication which may be a far field communication for example to begin transferring recharge energy at an instruction operation 608. For embodiments where there is a single recharge device 111 paired with the controller 102, then the controller 102 communicates with that recharge device 111. For instance, the patient or other user of the controller 102 may be aware that the patient, and hence the IMD 104, is in close proximity to the single recharge device 111 and may select an option to begin recharging and the controller 102 then sends the instruction. As another example, the controller 102 may continually query for the presence of the single recharge device 111 such as by using a communication key shared by both the controller 102 and the recharge device 111. Upon receiving a response from the recharge device 111, the controller 102 may then communicate with the single recharge device 111 to determine whether that single recharge device 111 is in proximity to the IMD 104 in order to determine whether to send the instruction to begin recharging.

Figure 8:
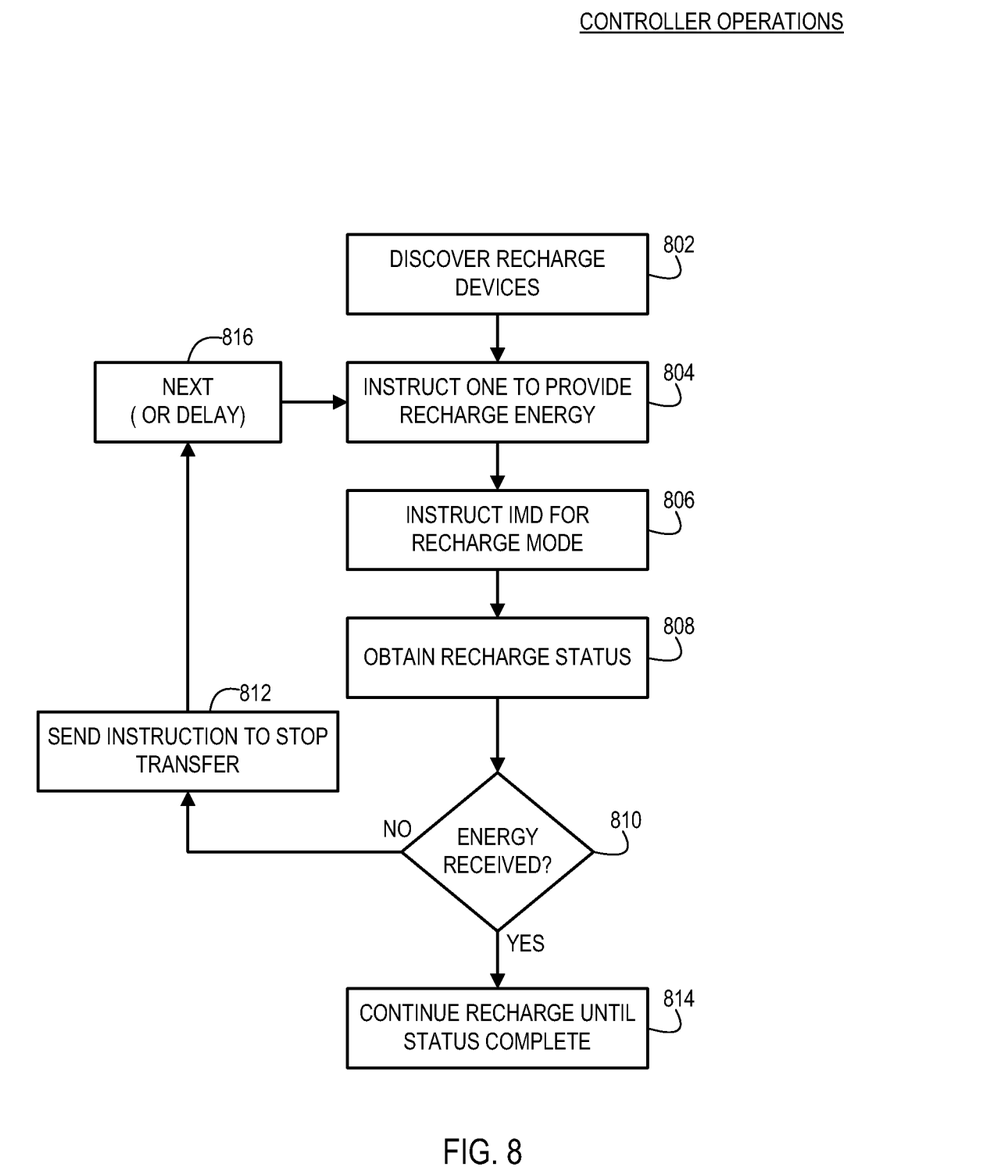
FIG. 8 shows a first example of operations of the external controller to initiate a recharge session with a particular recharge device.
Figure 9:
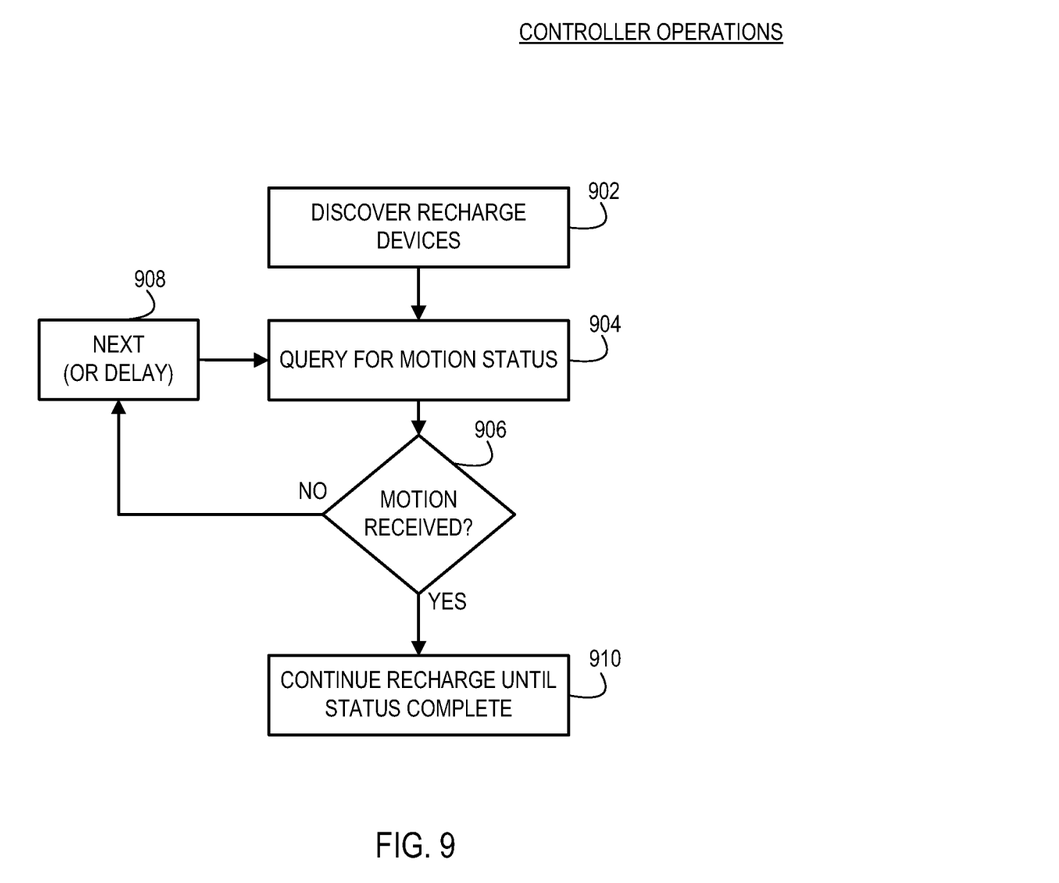
FIG. 9 shows a second example of operations of the external controller to initiate a recharge session with a particular recharge device.

FIGS. 8 and 9, discussed in more detail below, show logical operations allowing the controller 102 to make a determination about whether a particular recharge device 111 is appropriate for recharging and may use those operations to determine whether a single recharge device 111 is appropriately in proximity to begin recharging. Furthermore, the controller 102 may poll for the presence of multiple recharge devices 111 that may be present and may then utilize the operations of FIG. 8 and/or 9 to determine which recharge device 111 of the plurality that are present is the most appropriate to begin providing recharge energy to the IMD 104 at any given time.

As an alternative to the controller 102 communicating directly with the recharge device 111 at the instruction operation 108, the controller 102 may instead communicate directly with the IMD 104 to communicate the recharge instruction. The IMD 104 may have an established communication link with the recharge device 111 or may create one. This communication link may be via proximal telemetry or may be via a far field communication session. In either case, the IMD 104 may then send the recharge instruction to the recharge device 111.

As an alternative to instructing the recharge device 111 to begin recharging, the recharge device 111 may be configured to automatically begin the recharging process upon detecting that an IMD 104 is in proximity, such as by periodically determining activating the recharge coil and determining whether a load is present, such as is discussed below with reference to FIG. 8. The controller 102 may then be used to turn the recharge process on or off in response to user input. Thus, the controller 102 may establish the communication link with the recharge device 111 at the communication operation for purposes of deactivating the transfer of recharge energy either immediately or at some point in the future as may be selected by the user.

Once the instruction to begin recharging has begun, the controller 102 may then detect whether it is time to check the recharging status of the IMD 104 at a query operation 610. Once it is time to check the recharging status of the IMD 104, the controller 102 then obtains recharge information from the IMD 104 by sending a request for the information over the wireless communication link at a communication operation 612. In some embodiments, this may call for a wake-up procedure where the IMD 104 may put the wireless communications, particularly far field communications, in a sleep mode between queries for the recharge status.

Upon obtaining the recharge status information, the controller 102 may detect whether the battery 314 is fully charged such as based on recharge status information including available battery voltage, battery impedance, amount of current passing to the battery 314 and so forth at a query operation 614. If the battery 314 is not fully charged, then the controller 102 then allows recharging to continue but provides an instruction to adjust the recharging if such an adjustment is needed at an adjustment operation 615. For instance, the controller 102 may request that the amount of energy be increased such as to shorten the time to complete the recharge or be decreased to prevent a harmful condition. The controller 102 again detects whether the time has come to check for recharge status at the query operation 610. If the battery 314 is fully charged, then the controller 102 then instructs the recharge device 111 to stop the transfer of recharge energy at an instruction operation 616 and instructs the IMD 104 to exit the recharge mode, for embodiments where such is appropriate, at an instruction operation 618. This instruction to the recharge device 111 to stop the transfer of recharge energy may be provided directly to the recharge device 111 where a direct communication link is established or may be provided to the IMD 104 which then provides the instruction to the recharge device 111 over an established communication link.

FIG. 7A shows the operations of the controller 102 where the recharge device 111 establishes a wireless communication link, either via far field or near field, with the IMD 104 that is intended to be recharged. Initially, the controller 102 instructs the appropriate recharge device 111 to begin transferring recharge energy at an instruction operation 702. As discussed above, where there is a single recharge device 111 paired to the controller 102, then the controller 102 sends this instruction to the recharge device 111. As also discussed above, this instruction may be sent on the basis of a user requesting recharge to begin in one example or may be sent on the basis of the controller 102 determining from wireless communications with the recharge device 111 that the recharge device is in proper proximity to the IMD 104 for purposes of recharging.

This instruction triggers the recharge device 111 to establish communications with the IMD 104 and to instruct the IMD 104 to enter the recharge mode if appropriate. These communications may be via a far field communication link where both the recharge device 111 and the IMD 104 are equipped to do so. These communications may alternatively be via a near field communication link which may use the same telemetry head 109 that is also being used to transfer the recharge energy.

Once recharging has begun, the controller 102 may then detect whether it is time to check the recharging status of the IMD 104 at a query operation 704. Once it is time to check the recharging status of the IMD 104, the controller 102 then obtains recharge information from the IMD 104 by sending a request for the information over the wireless communication link with the recharge device 111 at a communication operation 706. This triggers the recharge device 111 to request this information from the IMD 104 including waking up the IMD 104 from a sleep mode if necessary, and then to report that information to the controller 102 upon receiving it from the IMD 104. In some embodiments, this may call for a wake-up procedure where the IMD 104 may put the wireless communications, particularly far field communications, in a sleep mode between queries for the recharge status.

Upon obtaining the recharge status information, the controller 102 may detect whether the battery 314 is fully charged such as based on recharge status information including available battery voltage, battery impedance, amount of current passing to the battery 314 and so forth at a query operation 708. If the battery 314 is not fully charged, then the controller 102 then allows recharging to continue and again detects whether the time has come to check for recharge status at the query operation 704. If the battery 314 is fully charged, then the controller 102 then instructs the recharge device 111 to stop the transfer of recharge information at an instruction operation 710. This triggers the recharge device 111 to terminate the communication session with the IMD 104 and to instruct the IMD 104 to exit the recharge mode if appropriate.

Figure 7B:
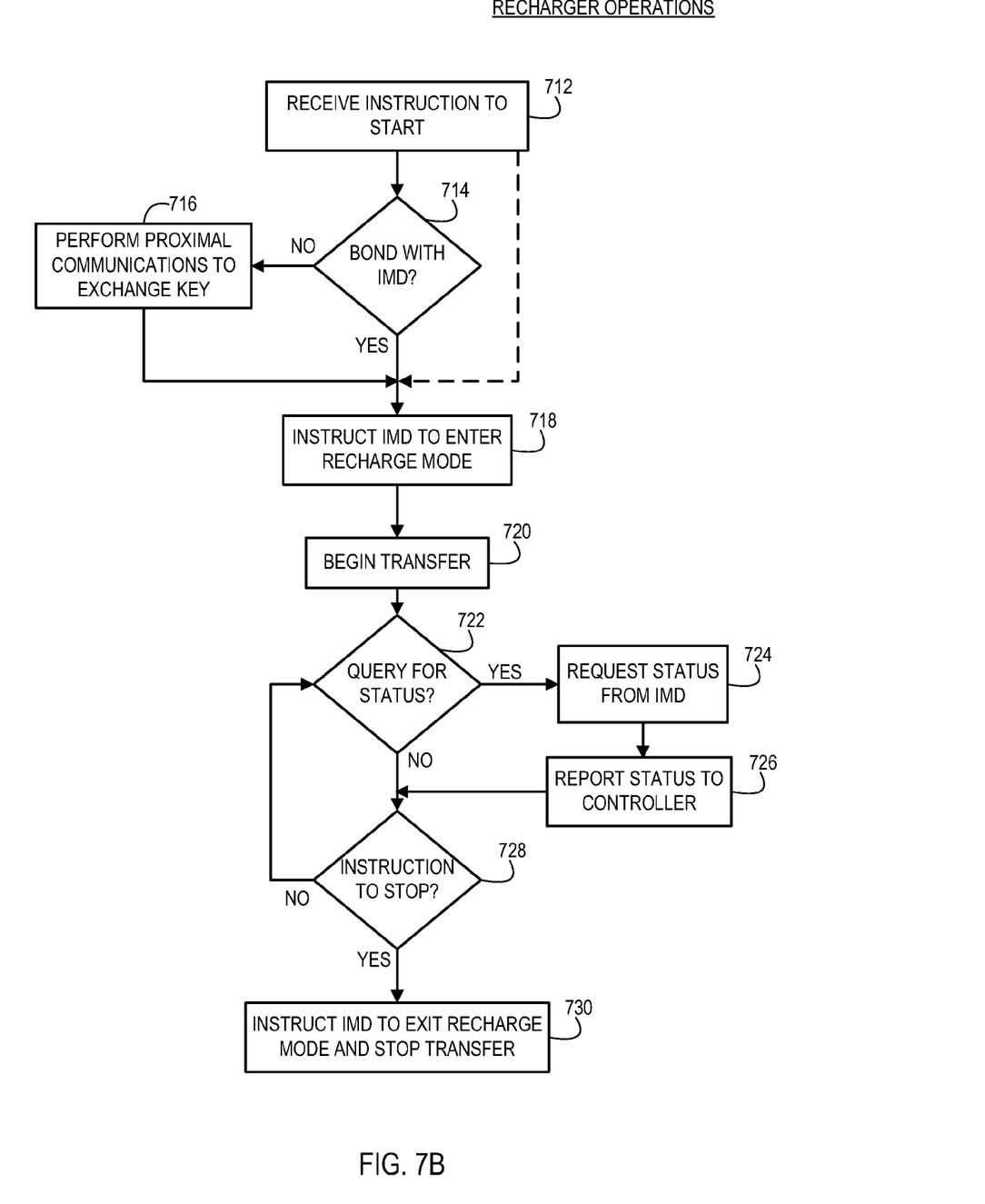
FIG. 7B shows an example of operations of the external recharge device to provide recharge energy during a recharge session.

FIG. 7B shows logical operations of the recharge device 111 that is working in conjunction with the controller 102 performing the logical operations of FIG. 7A. In such a case, the controller 102 may not communicate directly with the IMD 104 but may rely on the recharger 111 to communicate with the IMD 104 and then relay information between the controller 102 and the IMD 104.

Alternatively, these operations of FIG. 7B may work in conjunction with the logical operations of FIG. 6 such as where the controller 102 communicates with both the IMD 104 and the recharger 111 via the operations of FIG. 6, while the recharger 111 communicates with the controller 102 and the IMD 104 via the operations of FIG. 7B. In such an example, the recharger 111 may communicate with the IMD 104 to monitor the status of the recharge coupling between the two which the recharger 111 may then report this recharge status information to the controller 102 and then receive instructions to adjust output power and the like. Meanwhile the controller 102 may communicate directly with the IMD 104 to monitor recharge status information of the IMD 104 such as the battery status in order to ultimately control the recharge process and to also store relevant data about the recharge process within the IMD 104 which may be later obtained and reviewed by a clinician.

In FIG. 7B, the recharge device 111 may continually listen for and eventually receive the instruction to begin transferring recharge energy at the instruction operation 712. For embodiments where the communication link from the recharge device 111 to the IMD 104 is a far field link, the recharge device 111 may then proceed to discover IMDs and then determine whether the IMD involved in the far field communications is bonded to the recharge device 111 and/or whether that IMD is the intended IMD 104 at a query operation 714.

If the IMD being communicated with via the far field communications is not already bonded as it does not have a communication key already shared with it by the recharge device 111, the recharge device 111 may then initiate proximal communications at communication operation 716. Here the recharge device 111 can detect whether the IMD 104 which is receiving the proximal communications is also receiving the far field communications to confirm that the far field communications are with the correct IMD 104. Once that has been confirmed, the recharge device 111 may then share the communication key with the IMD 104 such as over the proximal communication link so as to create the bond with the IMD 104.

In some embodiments, the recharge device 111 sends an instruction to the IMD 104 to enter a recharge mode at an instruction operation 718 so that the IMD 104 may begin receiving recharge energy and allowing it to pass through any rectification, filters, regulators and the like and ultimately to the battery 314. In some embodiments, the IMD 104 may be configured to always receive transferred energy to send to the battery 314 such that the instruction operation 718 is not implemented. Furthermore, for embodiments where the recharge device 111 is already bonded to the IMD 104 or where near field communications are used, the logical operations may start at the instruction operation 718 or may start at a subsequent operation such as where the IMD 104 is always configured to receive the transfer of energy.

The subsequent operation for the recharge device 111 is to begin transferring recharge energy at a recharge operation 720. Once the recharging has begun, the recharge device 111 may then detect whether it is time to check the recharging status of the IMD 104 at a query operation 722. Once it is time to check the recharging status of the IMD 104, the recharge device 111 then obtains recharge information from the IMD 104 by sending a request for the information over the wireless communication link such as a far field communication link at a communication operation 724. In some embodiments, this may call for a wake-up procedure where the IMD 104 may put the wireless communications in a sleep mode between queries for the recharge status.

Upon obtaining the recharge status information, the recharge device 111 then reports that status information via the wireless communication link with the controller 102 at a communication operation 726. The controller 102 may then detect whether the battery 314 is fully charged such as based on recharge status information including available battery voltage, battery impedance, amount of current passing to the battery 314 and so forth. At the query operation 728, the recharge device 111 detects whether the controller 102 has responded with an instruction to stop providing the recharge energy. If the battery 314 is not fully charged, then the controller 102 will not send the instruction to stop and the recharge device 111 then allows recharging to continue and again detects whether the time has come to check for recharge status at the query operation 722. If the battery 314 is fully charged, then the controller 102 then instructs the recharge device 111 to stop the transfer of recharge information and the recharge device 111 stops the transfer of energy and instructs the IMD 104 to exit the recharge mode, for embodiments where such is appropriate, at a recharge operation 730.

FIG. 8 shows logical operations of the controller 102 where multiple recharge devices 111 are available and a selection of the most appropriate recharge device is desired and/or where a single recharge device 111 is available and automatically initiating recharge is desired. Initially, the controller 102 discovers the single recharge device 111 or multiple recharge devices 111 that are available over a wireless communication link at a discovery operation 802. The controller 102 receives responses to the discovery request and may select a response to establish a wireless session with the responding device or may establish a wireless session with each responding device such as where the wireless communication link is a far field link.

The controller 102 then instructs a recharge device 111 of one of the sessions to provide recharge energy at an instruction operation 804. The controller 102 then instructs the IMD 104 to enter the recharge mode, after having established wireless communications with the correct IMD 104 at an instruction operation 806. The controller 102 obtains the recharge status from the IMD 104 at a status operation 808. The controller 102 then detects whether the IMD 104 is receiving recharge energy at a query operation 810. If the IMD 104 is not receiving recharge energy, then presumably the recharge device 111 that has been instructed to provide the recharge energy is not the most appropriate one as it is not in proximity to the IMD 104.

The controller 102 then instructs the current recharge device 111 to stop transferring energy at an instruction operation 812 and switches to the communication session of the next recharge device 111 that has been discovered at operation 816. In the case of the single recharge device 111 that has been discovered, the controller merely delays for a preset period of time at operation 816. The controller 102 then instructs the next recharge device 111, or again instructs the single recharge device 111, to begin transferring recharge energy at instruction operation 808, and the operational flow proceeds as described above.

Upon the controller 102 detecting that energy is being received by the IMD 104 at the query operation 810, then controller 102 then allows the recharging to continue until the recharge status is a fully charged battery 314 at a recharge operation 814. The recharge operation 814 may correspond to the operations 610-618 of FIG. 6.

FIG. 9 shows another example of logical operations of the controller 102 where multiple recharge devices 111 are available and a selection of the most appropriate recharge device is desired and/or where a single recharge device 111 is available and automatically initiating recharge is desired. Initially, the controller 102 discovers the single recharge device 111 or multiple recharge devices 111 that are available over a wireless communication link at a discovery operation 902. The controller 102 receives responses to the discovery request and may select a response to establish a wireless session with the responding device or may establish a wireless session with each responding device where the wireless sessions are far field sessions.

The controller 102 then queries via a wireless communication a recharge device 111 of one of the sessions to provide status regarding motion of the recharge device 111 and receives that information at a request operation 904. The recharge device 111 collects information representative of motion from the accelerometer, 410, 512. The controller 102 then detects whether the current recharge device 111 has motion representative of being positioned in proper proximity to the patient at a query operation 906. Presumably if the recharge device 111 is experiencing motion over a preset threshold indicative of proximity to the patient, then the recharge device 111 is appropriately positioned for delivering recharge energy to the IMD 104 of the patient.

Where the motion status of the current recharge device 111 does not indicate proximity to the patient, then controller 102 switches to the communication session of the next recharge device 111 that has been discovered at operation 908. In the case of the single recharge device 111 that has been discovered, the controller merely delays for a preset period of time at operation 908. The controller 102 then queries the next recharge device 111, or again queries the single recharge device 111, to report the motion status at the request operation 904, and the operational flow proceeds as described above.

Upon the controller 102 detecting that the current recharge device 111 is experiencing motion indicative of proximity to the patient, then the controller 102 instructs that the transfer of energy begins and that recharging mode be entered where appropriate until the recharge is complete at a recharge operation 910. The recharge operation 910 may correspond to the operations 606-618 of FIG. 6.

In addition to or as an alternative to checking for motion, the controller 102 may also query the recharge device 111 to determine if the recharge device 111 is experiencing a load upon attempting to transfer recharge energy at the query operation 906. In some cases, a load may indicate that the recharge device 111 is inductively coupled to the IMD 104 and is appropriate for providing recharge energy. However, a load may be the result of an inductive coupling to another object. Similarly, motion of the recharge device 111 may be the result of something other than proximity to the patient. Thus, the presence of a load and the presence of motion of the recharge device 111 that is typical for being in proximity to the patient may provide a more accurate conclusion that the recharge device 111 is in proximity to the patient.

Some embodiments of the IMD 104 may employ both the operations of FIG. 8 and those of FIG. 9 to further confirm that a particular recharge device 111 is appropriate. For instance, the controller 102 may first determine whether the IMD 104 is receiving recharge energy as in FIG. 8, such as where the controller 102 instructs all recharge devices 111 to begin transferring energy at the same time. If the IMD 104 is receiving recharge energy, then the controller 102 may then detect which recharge device 111 is providing it by querying each recharge device 111 for motion indicative of proximity to the patient and/or for a load indicative of an inductive coupling to the IMD 104.

In relation to FIGS. 8 and 9, the recharge operations 814 and 910 may include repeating the detection of whether the IMD 104 is continuing to receive recharge energy as in FIG. 8 or whether the motion of the recharge device 111 continues to meet the threshold regarding proximity to the patient as in FIG. 9. Where the controller 102 detects that the recharge device 111 that is currently providing recharge energy is no longer the appropriate recharge device 111 due to a lack of energy being transferred or a lack of motion indicative of proximity to the patient, then the controller 102 may communicate with the current recharge device 111 to stop the transfer of energy even though the battery 314 was not fully charged.

Furthermore, the controller 102 may immediately begin communicating with other recharge devices 111 that may have been discovered to test each one for the proper transfer of energy to the IMD 104 and/or for the an adequate level of motion indicative of proximity to the IMD 104. In this manner, the patient with the IMD 104 may move about during the recharge process such that the controller 102 may allow recharging to continue by activating and deactivating recharge devices 111 that the patient may encounter. For example, the patient may have recharge devices 111 located at several locations within the home of the patient, and the patient may move from area to area within the home while recharging continues by utilizing the most appropriate recharge device 111 within the home at any given time.

A specific example of the system including the controller 102, recharge device 111, and IMD 104 is now described. The description of this specific example is for illustrative purposes and is not intended to be limiting with respect to any aspect of the recharging process and the interaction between the controller 102, the recharger 111, and the IMD 104.

The controller 102 of this example employs a Bluetooth transceiver as well as a MICS transceiver. The controller 102 also includes a touch screen for providing a user interface display. The controller 102 includes button controls that receive selections by the user.

The recharger 111 of this example is a single unit having a disk shape that encloses the recharge coil. The recharger 111 has Bluetooth communication and electronics to control recharge levels to the recharge coil, and the recharger 111 communicates only with the controller 102. The recharger 111 as a port that plugs into a docking station, which is where the recharger is placed by the user when not recharging the IMD 104. This docking station recharges the batteries within the recharger 111 and keeps the battery charged until a recharge session occurs.

When on the docking station, the recharger 111 does not start a recharge session but provides information via Bluetooth to the controller 111 about the status of the on-board batteries. The recharger 111 may be made less expensive and more rugged by omitting a user interface. The controller 102 can provide all information to the user regarding the recharge process. To bond the controller 102 to a recharger 111, the recharger 111 is placed in the docking station, and a button on the docking station is pressed to initiate Bluetooth discovery between the controller 104 and all the rechargers 111 in the docking station where there may be more than one.

Whenever the recharger 111 is out of the docking station, the recharger 111 will actively look for an IMD 104 to recharge. The recharger 111 may use loading of the recharge coil to determine if a metal object such as an IMD 104 is close. If close enough so that the controller 102 is in communication range, the recharger 111 tells the controller 102 that the recharger 111 has found something to recharge and that the recharger 111 is ready to begin recharging. The controller 102 attempts to communicate with the IMD 104 and if successful, the controller 102 initiates the recharge process on the recharger 111 and monitors the current entering into the IMD 104. The controller 102 may then provide feedback to the user regarding how well coupled the recharger 111 is to the IMD 104. If the controller 102 cannot communicate with the IMD 104, the controller 102 tells the user that the IMD 104 is not found and asks if the user wants to recharge anyway. This covers the situation where the IMD 104 is fully depleted and cannot communicate. If the user agrees, the controller 102 starts the recharge session and attempts to gain communication with the IMD 104 while recharge is occurring. The controller 102 ends the recharge session and notifies the user if, after several minutes, the IMD 104 still has not started to communicate.

During the recharge session, the recharger 111 provides antenna temperature information and recharger settings and measurements to the controller 104. Meanwhile, the IMD 104 stores information about the recharge diagnostics measured by the IMD 104, such as recharge current, length of recharge, and battery voltage. The controller 102 retrieves all the necessary information about recharging from the IMD 104 via the MICS band communications and from the recharger 111 via the Bluetooth® connection to allow the controller 102 to adjust the recharge via a return Bluetooth® communication to the recharger 111. In this manner, the recharger 111 has no need to communicate directly with the IMD 104, which simplifies the design of the recharger 111.

The controller 102 controls the settings of the recharger 111 to manage the energy output of the recharger 111 based on recharge data. The goal of the controller 102 is to limit the heat generated from the recharging session and to inform the user about how well the recharge session is performing.

While embodiments have been particularly shown and described, it will be understood by those skilled in the art that various other changes in the form and details may be made therein without departing from the spirit and scope of the invention.

What is claimed is:

1. A method of recharging an implantable medical device, comprising:
    initiating wireless communications between a first controller and a first recharge device that provide first recharge instructions from the first controller to the first recharge device to control recharging;
    transferring recharge energy from the first recharge device to the implantable medical device in accordance with the first recharge instructions;
    initiating wireless communications between the first controller and a second recharge device that provide second recharge instructions from the first controller to the second recharge device to control recharging; and
    transferring recharge energy from the second recharge device to the implantable medical device in accordance with the second recharge instructions.

2. The method of claim 1, wherein the wireless communications between the first controller and the first recharge device are far field communications.

3. The method of claim 2, wherein the far field communications have a frequency of at least 400 Megahertz.

4. The method of claim 2, wherein the far field communications have a frequency of at least 2400 Megahertz.

5. The method of claim 1, further comprising:
    initiating wireless communications between the first controller and the implantable medical device to obtain recharge status information from the implantable medical device; and
    generating the first recharge instructions at the first controller based on the recharge status information.

6. The method of claim 5, wherein the wireless communications between the first controller and the implantable medical device are far field communications.

7. The method of claim 1, further comprising:
    initiating wireless communications between the first recharger and the implantable medical device to obtain recharge status information from the implantable medical device, wherein the wireless communications between the first controller and the first recharge device provide the recharge status information from the first recharge device to the first controller; and
    generating the first recharge instructions at the first controller based on the recharge status information from the recharge device.

8. The method of claim 7, wherein the wireless communications between the first recharger and the implantable medical device are far field communications.

9. The method of claim 7, further comprising:
    initiating wireless communications between the controller and the implantable medical device to obtain recharge status information from the implantable medical device; and
    generating the first recharge instructions at the first controller based on the recharge status information from the implantable medical device.

10. The method of claim 7, wherein the wireless communications between the first recharger and the implantable medical device are near field communications.

11. The method of claim 1, further comprising:
    sensing by the first controller the presence of the first recharge device;
    in response to sensing the presence of the first recharge device, initiating the wireless communications between the first controller and the first recharge device.

12. A medical system, comprising:
    a first controller having a wireless communication circuit;
    a first recharge device having a wireless communication circuit in wireless communication with the wireless communication circuit of the first controller and having a wireless recharge circuit, the first recharge device receives first recharge instructions from the first controller and generates recharge energy in the recharge circuit based on the first recharge instructions;
    an implantable medical device having a wireless recharge circuit having wireless coupling to the wireless recharge circuit of the first recharge device to receive recharge energy from the first recharge device; and
    a second recharge device having a wireless communication circuit and a wireless recharge circuit, the controller initiates wireless communications with the second recharge device that provide second recharge instructions from the first controller to the second recharge device to control recharging, and wherein the second recharge device transfers recharge energy to the implantable medical device in accordance with the second recharge instructions through a coupling of the wireless recharge circuit of the second recharge device and the wireless recharge circuit of the implantable medical device.

13. The medical system of claim 12, wherein the wireless communication circuit of the first controller is a far field communication circuit and wherein the wireless communication circuit of the first recharge device is a far field communication circuit.

14. The medical system of claim 12, wherein the wireless communication circuit of the second recharge device is a far field communication circuit.

15. The medical system of claim 12, wherein the first controller initiates wireless communications with the implantable medical device to obtain recharge status information from the implantable medical device, and wherein the first controller generates the first recharge instructions based on the recharge status information.

16. The medical system of claim 15, wherein the implantable medical device includes a wireless far field communication circuit and wherein the wireless communications initiated by the first controller with the implantable medical device are far field communications.

17. The medical system of claim 12, wherein the first recharge device initiates wireless communications with the implantable medical device to obtain recharge status information from the implantable medical device, wherein the wireless communications between the first controller and the first recharge device provide the recharge status information from the first recharge device to the first controller, and wherein the first controller generates the first recharge instructions based on the recharge status information from the first recharger.

18. The medical system of claim 17, wherein the implantable medical device includes a wireless far field communication circuit and wherein the wireless communications initiated by the first recharger with the implantable medical device are far field communications.

19. The medical system of claim 17, wherein the controller initiates wireless communications with the implantable medical device to obtain recharge status information from the implantable medical device, and wherein the first controller generates the first recharge instructions based on the recharge status information from the implantable medical device.

20. The medical system of claim 17, wherein the wireless communication circuit of the first controller is a far field communication circuit and wherein the wireless communication circuit of the first recharge device is a far field communication circuit.

21. The medical system of claim 12, wherein the first controller senses the presence of the first recharge device and in response to sensing the presence of the first recharge device, initiates the wireless communications with the first recharge device.

* * * * *